United States Patent
Jiang et al.

(10) Patent No.: US 8,513,405 B2
(45) Date of Patent: Aug. 20, 2013

(54) REAGENT, CHAOTROPIC AGENT, AND REAGENT KIT FOR AND APPLICATIONS OF ISOLATING NUCLEIC ACID BY USE OF MAGNETIC CELLULOSE MATERIAL

(75) Inventors: Pei-Shin Jiang, Xindian (TW); Yu-Ting Su, Xindian (TW); Kun-Chan Wu, Xindian (TW); Hui-Ju Cho, Xindian (TW); Wen-Hsun Kuo, Xindian (TW); Yuh-Jiuan Lin, Xindian (TW); Yi-Ling Li, Xindian (TW); Cheng-Chun Kuan, Xindian (TW)

(73) Assignee: RBC Bioscience Corp., Taipei County (TW)

( * ) Notice: Subject to any disclaimer, the term of this patent is extended or adjusted under 35 U.S.C. 154(b) by 205 days.

(21) Appl. No.: 12/935,681

(22) PCT Filed: Apr. 2, 2008

(86) PCT No.: PCT/CN2008/000669
§ 371 (c)(1),
(2), (4) Date: Mar. 16, 2011

(87) PCT Pub. No.: WO2009/121208
PCT Pub. Date: Oct. 8, 2009

(65) Prior Publication Data
US 2011/0166338 A1    Jul. 7, 2011

(51) Int. Cl.
*C07H 21/02* (2006.01)
*C07H 21/00* (2006.01)

(52) U.S. Cl.
USPC .............. 536/25.4; 536/25.41; 536/25.42

(58) Field of Classification Search
None
See application file for complete search history.

(56) References Cited

U.S. PATENT DOCUMENTS

| | | |
|---|---|---|
| 5,990,302 A | 11/1999 | Kuroita et al. |
| 6,855,499 B1 | 2/2005 | Nargessi |
| 7,868,145 B2 * | 1/2011 | Wu et al. ............ 530/412 |

* cited by examiner

*Primary Examiner* — Lawrence E Crane
(74) *Attorney, Agent, or Firm* — Ming Chow; Sinorica, LLC

(57) ABSTRACT

Disclosed are a chaotropic agent; a reagent including a chaotropic agent and a lithium salt; a reagent kit including a chaotropic agent; a chaotropic agent, a reagent, a reagent kit, and a method for isolating a nucleic acid by use of a magnetic cellulose material; a method for binding a nucleic acid to a magnetic cellulose material; a method for isolating a nucleic acid; and a method for purifying a chromosome DNA. It is required that each of the chaotropic agents, the reagents, and the reagent kits works with at least one solid-phase, magnetic cellulose-containing carrier to isolate a nucleic acid from non-nucleic acid substances. In addition, each chaotropic agent includes an alcohol substance and a substrate solution for adjusting the alcohol substance to an appropriate concentration and thereby promoting binding of the nucleic acid in a sample to the magnetic cellulose.

15 Claims, No Drawings

REAGENT, CHAOTROPIC AGENT, AND REAGENT KIT FOR AND APPLICATIONS OF ISOLATING NUCLEIC ACID BY USE OF MAGNETIC CELLULOSE MATERIAL

CROSS-REFERENCE TO RELATED APPLICATION

This application is a National Stage application under 35 USC §371 claiming the benefit and priority with respect to PCT Application No. PCT/CN2008/000669, filed on Apr. 2, 2008. The related application is incorporated by reference herein in their entirety.

BACKGROUND OF THE INVENTION

1. Technical Field

The present invention relates to a chaotropic agent, a reagent, a reagent kit, and an isolation method. More particularly, the present invention relates to a chaotropic agent, a reagent, a reagent kit, and a method for isolating a nucleic acid.

2. Description of Related Art

Conventionally, a nucleic acid is isolated from a nucleic acid-containing sample and purified by denaturing the protein and other substances in the sample using an organic solvent such as phenol and chloroform, and then performing centrifugation so that the denatured protein and substances are separated from the nucleic acid. However, as both phenol and chloroform are highly corrosive, highly volatile, and highly toxic, the aforesaid operation must be conducted with great care; otherwise, the operator is very likely to be injured. In addition, the purification process of this conventional method is time-consuming and therefore poses difficulties in commercial use.

Currently, the nucleic acid isolation methods used in commercial applications are mostly based on the patented particle isolation technique (U.S. Pat. No. 5,234,809) developed by Willem R. Boom et al. and assigned to Akzo Nobel N.V. In the afore-cited US patent, which is also known as the "Boom patent", a nucleic acid is isolated from the non-nucleic acid substances in a sample by means of a chaotropic agent. The isolated nucleic acid binds to silica particles and is then eluted therefrom by a washing buffer so as to recover the nucleic acid. Nevertheless, the development trend of nucleic acid isolation techniques after the "Boom patent" is toward the use of magnetic particles, which are more effective in separating a nucleic acid from non-nucleic acid substances, as disclosed in U.S. Pat. No. 6,855,499, or toward further improvement of the composition of chaotropic agents.

For instance, U.S. Pat. No. 5,990,302 teaches a method for isolating a nucleic acid from non-nucleic acid substances by means of a guanidine salt-containing chaotropic agent and a nucleic acid-binding carrier. However, effective isolation cannot be achieved unless the proportion of the guanidine salt with respect to the solvents used is properly controlled. Moreover, as the manufacture of the guanidine salt is complicated and requires a separate production line, the guanidine salt-containing chaotropic agent may be difficult to prepare in practice.

Hence, the development of a chaotropic agent that features effective nucleic acid isolation, safe operation, convenient use, and easy manufacture and of a reagent kit containing such a chaotropic agent remains a problem to be solved.

SUMMARY OF THE INVENTION

For overcoming the aforementioned shortcomings of the prior art, the present invention provides a chaotropic agent for use in conjunction with a solid-phase carrier to isolate a nucleic acid from non-nucleic acid substances. When the solid-phase carrier is added with the chaotropic agent and mixed with a sample containing the nucleic acid, the chaotropic agent provides isolation of the nucleic acid from non-nucleic acid substances in the sample and promotes binding and adsorption of the nucleic acid to the solid-phase carrier. The chaotropic agent is characterized in that the solid-phase carrier used with the chaotropic agent comprises magnetic cellulose. And the chaotropic agent comprises an alcohol substance and a substrate solution. The substrate solution adjusts the metal salt and the alcohol substance to appropriate concentrations and thereby promotes binding of the nucleic acid to the magnetic cellulose material. The alcohol substance can be ethanol, isopropanol, or an arbitrary combination of ethanol and isopropanol.

The present invention also provides a reagent for use in conjunction with a solid-phase carrier to isolate a nucleic acid from non-nucleic acid substances. When the solid-phase carrier is added with the reagent and mixed with a sample containing the nucleic acid, the reagent provides isolation of the nucleic acid from non-nucleic acid substances in the sample and promotes binding and adsorption of the nucleic acid to the solid-phase carrier. The reagent is characterized in that the solid-phase carrier used with the reagent comprises magnetic cellulose. And the reagent comprises a metal salt and a chaotropic agent. The chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a reagent kit for isolating a nucleic acid from non-nucleic acid substances. The reagent kit comprises a reagent, a solid-phase carrier for use with the reagent, a washing buffer, and an elution buffer. The reagent kit being characterized in that the solid-phase carrier comprises magnetic cellulose. And the reagent comprises a metal salt and a chaotropic agent. The chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a chaotropic agent for isolating a nucleic acid by use of a magnetic cellulose material. When the magnetic cellulose material is added with the chaotropic agent and mixed with a sample containing the nucleic acid, the chaotropic agent provides isolation of the nucleic acid from non-nucleic acid substances in the sample. The chaotropic agent is characterized in that the chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a reagent for isolating a nucleic acid by use of a magnetic cellulose material. When the magnetic cellulose material is added with the reagent and mixed with a sample containing the nucleic acid, the reagent provides isolation of the nucleic acid from non-nucleic acid substances in the sample. The reagent is characterized in that the reagent comprises a metal salt and a chaotropic agent. The chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a reagent kit for isolating a nucleic acid by use of a magnetic cellulose material. The reagent kit is characterized in that the reagent kit comprises a reagent, the magnetic cellulose material, a washing buffer, and an elution buffer. The reagent comprises a metal salt and a chaotropic agent. The chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a method for isolating a nucleic acid by use of a magnetic cellulose material. The method comprises steps of: providing a sample containing the nucleic acid, and preparing a reagent and the magnetic cellulose material for use with the reagent. The method is characterized by further comprising adding and mixing the reagent into the sample containing the nucleic acid The reagent comprises a metal salt and a chaotropic agent. The chaotropic agent comprises an alcohol substance and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a method for isolating a nucleic acid by use of a magnetic cellulose material. The method comprises steps of: providing a sample containing the nucleic acid, and preparing a reagent, the magnetic cellulose material for use with the reagent, a washing buffer, and an elution buffer. The method is characterized by further comprises: adding and mixing the reagent into the sample containing the nucleic acid. The reagent comprises a metal salt, an alcohol substance, and a substrate solution. The substrate solution adjusts the metal salt and the alcohol substance to appropriate concentrations and thereby promotes binding of the nucleic acid to the magnetic cellulose material. The metal salt can be univalent cations. The lithium salt, sodium salt, or potassium salt is proffered. The alcohol can be ethanol, isopropanol, or an arbitrary combination of ethanol and isopropanol. The method further comprises steps of washing the magnetic cellulose material with the washing buffer to remove non-nucleic acid substances in the sample; and isolating the nucleic acid from the magnetic cellulose material to which the nucleic acid has bound, with the elution buffer.

The present invention also provides a method for binding a nucleic acid to a magnetic cellulose material. The method comprises steps of: providing a sample containing the nucleic acid, and preparing a reagent and the magnetic cellulose material for use with the reagent. The method is characterized by further comprising: adding and mixing the reagent into the sample containing the nucleic acid. The reagent comprises a metal salt, an alcohol substance, and a substrate solution. The substrate solution adjusts the metal salt and the alcohol substance to appropriate concentrations and thereby promoting binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a method for binding a nucleic acid to a magnetic cellulose material. The method comprises steps of: providing a sample containing the nucleic acid, and preparing a reagent and the magnetic cellulose material for use with the reagent. The method is characterized by further comprising: adding and mixing the reagent into the sample containing the nucleic acid. The reagent comprises a metal salt, an alcohol substance, and a substrate solution. The substrate solution adjusts the metal salt and the alcohol substance to appropriate concentrations and thereby promotes binding of the nucleic acid to the magnetic cellulose material. The metal salt can be the salt made of univalent cations. The lithium salt, sodium salt, or potassium salt is proffered. The alcohol can be ethanol, isopropanol, or an arbitrary combination of ethanol and isopropanol.

The present invention also provides a method for isolating a nucleic acid. The method comprises steps of: providing a sample containing the nucleic acid, and preparing a washing buffer and an elution buffer. The method is characterized by further comprising:

(a) provide a solid-phase carrier, and the solid-phase carrier comprises magnetic cellulose;

(b) provide a reagent, and the reagent comprises a metal salt, an alcohol substance, and a substrate solution, the substrate solution adjusting the metal salt and the alcohol substance to appropriate concentrations and thereby promoting binding of the nucleic acid in the sample to the solid-phase carrier, the metal salt having a univalent cation, the alcohol substance being selected from the group consisting of ethanol, isopropanol, and an arbitrary combination of ethanol and isopropanol; and (c) mixing the reagent with the solid-phase carrier and the sample containing the nucleic acid, washing the solid-phase carrier with the washing buffer to remove non-nucleic acid substances in the sample, and isolating the nucleic acid from the solid-phase carrier to which the nucleic acid has bound, with the elution buffer.

The present invention also provides a method for purifying a chromosome DNA, comprising steps of: providing a sample containing the chromosome DNA, and preparing a washing buffer and an elution buffer, the method being characterized by further comprising:

(a) providing a solid-phase carrier, wherein the solid-phase carrier comprises magnetic cellulose;

(b) providing a reagent, wherein the reagent comprises a metal salt, an alcohol substance, and a substrate solution, the substrate solution adjusting the metal salt and the alcohol substance to appropriate concentrations and thereby promoting binding of the chromosome DNA in the sample to the solid-phase carrier, the metal salt having a univalent cation, the alcohol substance being selected from the group consisting of ethanol, isopropanol, and an arbitrary combination of ethanol and isopropanol; and (c) mixing the reagent with the solid-phase carrier and the sample containing the chromosome DNA, washing the solid-phase carrier with the washing buffer to remove non-nucleic acid substances in the sample, and isolating the chromosome DNA from the solid-phase carrier to which the chromosome DNA has bound, with the elution buffer.

Therefore, the primary object of the present invention is to provide a chaotropic agent that feature effective nucleic acid isolation for use in conjunction with a solid-phase carrier to isolate a nucleic acid from non-nucleic acid substances.

Another object of the present invention is to provide a chaotropic agent that features safe operation and convenient use for use in conjunction with a solid-phase carrier to isolate a nucleic acid from non-nucleic acid substances.

Still another object of the present invention is to provide a chaotropic agent that features easy manufacture for use in conjunction with a solid-phase carrier to isolate a nucleic acid from non-nucleic acid substances.

Therefore, the primary object of the present invention is to provide a reagent that feature effective nucleic acid isolation for use in conjunction with a solid-phase carrier to isolate a nucleic acid from non-nucleic acid substances.

Another object of the present invention is to provide a reagent that features safe operation and convenient use for use in conjunction with a solid-phase carrier to isolate a nucleic acid from non-nucleic acid substances.

Still another object of the present invention is to provide a reagent that features easy manufacture for use in conjunction with a solid-phase carrier to isolate a nucleic acid from non-nucleic acid substances.

Therefore, the primary object of the present invention is to provide a reagent kit that feature effective nucleic acid isolation.

Another object of the present invention is to provide a reagent kit that features safe operation and convenient use.

Still another object of the present invention is to provide a reagent kit that features easy manufacture.

Therefore, the primary object of the present invention is to provide a chaotropic agent that feature effective nucleic acid isolation for isolating a nucleic acid by use of a magnetic cellulose material.

Another object of the present invention is to provide a chaotropic agent that features safe operation and convenient use for isolating a nucleic acid by use of a magnetic cellulose material.

Still another object of the present invention is to provide a chaotropic agent that features easy manufacture for isolating a nucleic acid by use of a magnetic cellulose material.

Therefore, the primary object of the present invention is to provide a reagent that feature effective nucleic acid isolation for isolating a nucleic acid by use of a magnetic cellulose material.

Another object of the present invention is to provide a reagent that features safe operation and convenient use for isolating a nucleic acid by use of a magnetic cellulose material.

Still another object of the present invention is to provide a reagent that features easy manufacture for isolating a nucleic acid by use of a magnetic cellulose material.

Therefore, the primary object of the present invention is to provide a reagent kit that feature effective nucleic acid isolation for isolating a nucleic acid by use of a magnetic cellulose material.

Another object of the present invention is to provide a reagent kit that features safe operation and convenient use for isolating a nucleic acid by use of a magnetic cellulose material.

Still another object of the present invention is to provide a reagent kit that features easy manufacture for isolating a nucleic acid by use of a magnetic cellulose material.

Therefore, the primary object of the present invention is to provide a method that feature effective nucleic acid isolation for isolating a nucleic acid by use of a magnetic cellulose material.

Another object of the present invention is to provide a method that features safe operation and convenient use for isolating a nucleic acid by use of a magnetic cellulose material.

Still another object of the present invention is to provide a method that features easy manufacture for isolating a nucleic acid by use of a magnetic cellulose material.

Therefore, the primary object of the present invention is to provide a method that feature effective nucleic acid isolation for binding a nucleic acid to a magnetic cellulose material.

Another object of the present invention is to provide a method that features safe operation and convenient use for binding a nucleic acid to a magnetic cellulose material.

Still another object of the present invention is to provide a method that features easy manufacture for binding a nucleic acid to a magnetic cellulose material.

Therefore, the primary object of the present invention is to provide a method that feature effective nucleic acid isolation for isolating a nucleic acid.

Another object of the present invention is to provide a method that features safe operation and convenient use for isolating a nucleic acid.

Still another object of the present invention is to provide a method that features easy manufacture for isolating a nucleic acid.

Therefore, the primary object of the present invention is to provide a method that feature effective nucleic acid isolation for purifying a chromosome DNA.

Another object of the present invention is to provide a method that features safe operation and convenient use for purifying a chromosome DNA.

Still another object of the present invention is to provide a method that features easy manufacture for purifying a chromosome DNA.

DETAILED DESCRIPTION THE INVENTION

The present invention provides a chaotropic agent, a reagent, a reagent kit, a chaotropic agent for isolating a nucleic acid by use of a magnetic cellulose material, a reagent for isolating a nucleic acid by use of a magnetic cellulose material, a reagent kit for isolating a nuclide acid by use of a magnetic cellulose material, a method for isolating a nucleic acid by use of a magnetic cellulose material, a method for binding a nucleic acid to a magnetic cellulose material, and a method for purifying a chromosome DNA, as described hereinafter with reference to some illustrative embodiments. Since the principles and basic schemes of the carrier/nucleic acid binding step, the nucleic acid isolation step, the washing step, and the elution program of the present invention are well known to a person of ordinary skill in the art, a detailed description of such principles and schemes is omitted herein.

Embodiment 1

Embodiment 1 of the present invention is a chaotropic agent which must be used in conjunction with a solid-phase carrier in order to isolate a nucleic acid from non-nucleic acid substances, such as to isolate a plasmid DNA, a genome DNA, a cDNA, or like DNA substances from a cell lysate, wherein the cell lysate can be derived from a culture solution containing cells or bacteria, a tissue sample, a whole blood sample, and so on.

The solid-phase carrier for use with the chaotropic agent is magnetic cellulose paper or magnetic cellulose beads made of magnetic cellulose. The method for making the magnetic cellulose paper or magnetic cellulose beads is based on the method proposed by M. Pourfarzaneh et al. (The Use of Magnetizable Particles in Solid Phase Immunoassay, M. Pourfarzaneh, R. S. Kamel, J. Landon, and C. C. Dawes, *Methods of Biochemical Analysis*. Volume 28, Page 267-295).

The chaotropic agent includes an alcohol substance and a substrate solution. The alcohol substance can be ethanol, isopropanol, and an arbitrary combination of ethanol and isopropanol. The substrate solution contains a lithium salt, sodium salt, or potassium salt having a concentration ranging from 0.05M to 2.0M. In addition, the substrate solution has a pH value ranging approximately from 5.0 to 7.5. A good isolation effect is attainable when the concentration of the alcohol substance is between about 10% and 80% by volume.

To isolate a DNA from non-nucleic acid substances in a sample, the chaotropic agent and the solid-phase carrier (i.e., the magnetic cellulose paper or magnetic cellulose beads made of magnetic cellulose) are added to the sample such that the sample is mixed with the solid-phase carrier. As the substrate solution adjusts the concentration of the alcohol substance to an appropriate level, the chaotropic agent breaks the hydrogen bonding, Van der Waals interactions, or hydrophobic effects between the nucleic acid and the environment in which the nucleic acid is located, thus isolating the DNA from the non-nucleic acid substances in the sample and allowing the DNA in the sample to bind and be adsorbed to the magnetic cellulose paper or magnetic cellulose beads. Detailed experiment results are presented further below in Comparative Example 1 and Comparative Example 2.

Embodiment 2

Embodiment 2 of the present invention is a reagent which, when used in nucleic acid isolation, can effectively isolate a nucleic acid from non-nucleic acid substances and result in adsorption of the nucleic acid to a solid-phase carrier. The reagent includes a lithium salt, sodium salt, or potassium salt of a predetermined concentration and a chaotropic agent, wherein the lithium salt, sodium salt, or potassium salt has a concentration ranging from 0.05M to 2.0M.

The reagent must be used in conjunction with a solid-phase carrier in order to isolate a nucleic acid from non-nucleic acid substances, such as to isolate a plasmid DNA, a genome DNA, a cDNA, or like DNA substances from a cell lysate, wherein the cell lysate can be derived from a culture solution containing cells or bacteria, a tissue sample, a whole blood sample, and so on.

The solid-phase carrier for use with the reagent is magnetic cellulose paper or magnetic cellulose beads made of magnetic cellulose by the method described in Embodiment 1.

The chaotropic agent includes an alcohol substance and a substrate solution. The alcohol substance can be ethanol, isopropanol, and an arbitrary combination of ethanol and isopropanol. In addition, the substrate solution has a pH value ranging approximately from 5.0 to 7.5. The substrate solution contains a lithium salt, sodium salt, or potassium salt having a concentration ranging from 0.05M to 2.0M. A good isolation effect is attainable when the concentration of the alcohol substance is between about 10% and 80% by volume.

To isolate a DNA from non-nucleic acid substances in a sample, the chaotropic agent and the solid-phase carrier (i.e., the magnetic cellulose paper or magnetic cellulose beads made of magnetic cellulose) are added to the sample such that the sample is mixed with the solid-phase carrier. As the substrate solution adjusts the concentration of the alcohol substance to an appropriate level, the chaotropic agent breaks the hydrogen bonding, Van der Waals interactions, or hydrophobic effects between the nucleic acid and the environment in which the nucleic acid is located, thus isolating the DNA from the non-nucleic acid substances in the sample and allowing the DNA in the sample to bind and be adsorbed to the magnetic cellulose paper or magnetic cellulose beads. Detailed experiment results are presented further below in Comparative Example 1 and Comparative Example 2.

Embodiment 3

Embodiment 3 of the present invention is a reagent kit for isolating a nucleic acid from non-nucleic acid substances and thereby recovering the nucleic acid. For instance, the reagent kit is suitable for isolating a plasmid DNA, a genome DNA, a cDNA, or like DNA substances from a cell lysate so as to recover the DNA substances.

The reagent kit includes a reagent, a solid-phase carrier for use with the reagent, a washing buffer, and an elution buffer. The reagent kit is characterized in that the solid-phase carrier for use with the reagent is magnetic cellulose paper or magnetic cellulose beads made of magnetic cellulose. In addition, the reagent of the reagent kit includes a metal salt having a univalent cation (e.g., a lithium salt, a sodium salt, or a potassium salt) and a chaotropic agent. The chaotropic agent includes an alcohol substance and a substrate solution. The alcohol substance can be ethanol, isopropanol, and an arbitrary combination of ethanol and isopropanol. The concentration of the lithium salt, sodium salt, or potassium salt, as well as the concentrations and pH values of the alcohol substance and the substrate solution, is the same as in Embodiment 2 and therefore is not repeated herein. The following two paragraphs describe only the unique features of the present embodiment.

To use the reagent kit, the reagent, which contains the metal salt with a univalent cation and the chaotropic agent, is added to a sample, along with the solid-phase carrier, which is in the form of magnetic cellulose paper or magnetic cellulose beads, such that the sample is mixed with the solid-phase carrier. The substrate solution adjusts the concentration of the alcohol substance to an appropriate level, allowing the chaotropic agent in the reagent to break the hydrogen bonding, Van der Waals interactions, or hydrophobic effects between the nucleic acid and the environment in which the nucleic acid is located, and thereby isolating the DNA from the non-nucleic acid substances in the sample. As a result, the DNA in the sample binds and is adsorbed to the magnetic cellulose paper or magnetic cellulose beads to form a complex.

The complex formed by the DNA and the magnetic cellulose paper or magnetic cellulose beads is washed with the washing buffer to remove impurities attached to the complex. After the washing is complete, the DNA is washed off the magnetic cellulose paper or magnetic cellulose beads by the elution buffer and elutes into the elution buffer. Thus, the DNA is recovered from the sample. Detailed experiment results are presented further below in Comparative Example 1 and Comparative Example 2.

Embodiment 4

Embodiment 4 of the present invention is a chaotropic agent for isolating a nucleic acid by use of a magnetic cellulose material, such as to isolate a plasmid DNA, a genome DNA, a cDNA, or like DNA substances from a cell lysate, wherein the cell lysate can be derived from a culture solution containing cells or bacteria, a tissue sample, a whole blood sample, and so on. The chaotropic agent includes an alcohol substance and a substrate solution. The alcohol substance can be ethanol, isopropanol, and an arbitrary combination of ethanol and isopropanol. The substrate solution contains a lithium salt, sodium salt, or potassium salt having a concentration ranging from 0.05M to 2.0M. In addition, the substrate solution has a pH value ranging approximately from 5.0 to 7.5. A good isolation effect is attainable when the concentration of the alcohol substance is between about 10% and 80% by volume.

To isolate a DNA from non-nucleic acid substances in a sample, the chaotropic agent and the solid-phase carrier (i.e., the magnetic cellulose paper or magnetic cellulose beads made of magnetic cellulose) are added to the sample such that the sample is mixed with the solid-phase carrier. As the substrate solution adjusts the concentration of the alcohol substance to an appropriate level, the chaotropic agent breaks the hydrogen bonding, Van der Waals interactions, or hydrophobic effects between the nucleic acid and the environment in which the nucleic acid is located, thus isolating the DNA from the non-nucleic acid substances in the sample and allowing the DNA in the sample to bind and be adsorbed to the magnetic cellulose paper or magnetic cellulose beads. Detailed experiment results are presented further below in Comparative Example 1 and Comparative Example 2.

Embodiment 5

Embodiment 5 of the present invention is a reagent for isolating a nucleic acid by use of a magnetic cellulose material. When used in nucleic acid isolation, the reagent can effectively isolate a nucleic acid from non-nucleic acid substances and cause adsorption of the nucleic acid to the magnetic cellulose material. The reagent includes a metal salt having a univalent cation (e.g., a lithium salt, sodium salt, or potassium salt) and a chaotropic agent wherein the lithium salt, sodium salt, or potassium salt has a concentration ranging from 0.05M to 2.0M.

The regent is to isolate a plasmid DNA, a genome DNA, a cDNA, or like DNA substances from a cell lysate, wherein the cell lysate can be derived from a culture solution containing cells or bacteria, a tissue sample, a whole blood sample, and so on.

The aforementioned chaotropic agent includes an alcohol substance and a substrate solution. The substrate solution contains a lithium salt, sodium salt, or potassium salt. A good isolation effect is attainable when the concentration of the alcohol substance is between about 10% and 80% by volume. The composition of alcohol substance and the pH value of the substrate solution is the same as in Embodiment 2 and therefore is not repeated herein.

To isolate a DNA from non-nucleic acid substances in a sample, the chaotropic agent and the solid-phase carrier (i.e., the magnetic cellulose paper or magnetic cellulose beads made of magnetic cellulose) are added to the sample such that the sample is mixed with the solid-phase carrier. As the substrate solution adjusts the concentration of the alcohol substance to an appropriate level, the chaotropic agent breaks the hydrogen bonding, Van der Waals interactions, or hydrophobic effects between the nucleic acid and the environment in which the nucleic acid is located, thus isolating the DNA from the non-nucleic acid substances in the sample and allowing the DNA in the sample to bind and be adsorbed to the magnetic cellulose paper or magnetic cellulose beads. Detailed experiment results are presented further below in Comparative Example 1 and Comparative Example 2.

Embodiment 6

Embodiment 6 of the present invention is a reagent kit for isolating a nucleic acid by use of a magnetic cellulose material. The reagent kit is designed to isolate a nucleic acid from non-nucleic acid substances and thereby recover the nucleic acid.

The reagent kit is characterized by including a reagent, a magnetic cellulose material, a washing buffer, and an elution buffer. The reagent of the reagent kit includes a metal salt having a univalent cation (e.g., a lithium salt, sodium salt, or potassium salt) and a chaotropic agent. The chaotropic agent includes an alcohol substance and a substrate solution, wherein the alcohol substance is selected from the group consisting of ethanol, isopropanol, and an arbitrary combination of ethanol and isopropanol. The concentration of the metal salt, as well as the concentrations and pH values of the alcohol substance and the substrate solution, is the same as in Embodiment 2 and therefore is not repeated herein. Described below are the unique features of the present embodiment.

To use the reagent kit, the reagent, which contains the metal salt with a univalent cation and the chaotropic agent, is added to a sample, along with the solid-phase carrier, which is in the form of magnetic cellulose paper or magnetic cellulose beads, such that the sample is mixed with the solid-phase carrier. The substrate solution adjusts the concentration of the alcohol substance to an appropriate level, allowing the chaotropic agent in the reagent to break the hydrogen bonding, Van der Waals interactions, or hydrophobic effects between the nucleic acid and the environment in which the nucleic acid is located, and thereby isolating the DNA from the non-nucleic acid substances in the sample. As a result, the DNA in the sample binds and is adsorbed to the magnetic cellulose paper or magnetic cellulose beads to form a complex.

Comparative Example 1

Tests were conducted to evaluate the effectiveness of the foregoing embodiments (i.e., the chaotropic agent; the reagent and the reagent kit containing the chaotropic agent; the chaotropic agent for use with a magnetic cellulose material, etc.) in isolating a nucleic acid from non-nucleic acid substances and in promoting binding of the nucleic acid to the magnetic cellulose material. More specifically, a fixed amount of nucleic acid was used as the starting sample. Added to the starting sample were different metal salts and an alcohol substance whose total volume and concentrations were fixed and a magnetic cellulose material. The nucleic acid content of the sample was measured in each step of the test to determine the binding effect and the final recovery rate. A detailed description of the steps is given below:

1. Prepare 200 µl of 50 mg/ml human placenta DNA (Sigma D7011).

2. Into the human placenta DNA of Step 1, add 500 µl of chaotropic agent or reagent and 20 µl of Cortex Cellulose beads (Megacell™), wherein the chaotropic agent or reagent contains 72% ethanol (EtOH) and a 0.05M metal salt, with the metal salt varying from test to test. Mix thoroughly and allow the mixture to rest at room temperature for 10 min.

3. Remove the supernatant after the DNA-bound beads precipitate, and measure the absorbance of the supernatant at 260 nm (i.e., O.D.260). The absorbance value is converted into DNA concentration and hence DNA content. The DNA content is compared with the starting DNA content to determine the isolation effect. (Isolation effect=1−Binding effect)

4. Wash with 500 µl of 70% isopropanol as the washing buffer. Then, rinse the DNA off the beads with 20 µl of water. Measure the recovered DNA content, and compare it with the starting DNA content to determine the recovery rate.

As shown in Table 1, 0.05M lithium chloride (LiCl), sodium acetate (NaOAc), and sodium chloride (NaCl) were used as the metal salt solution in the foregoing embodiments to work in combination with 72% ethanol. In the control group (i.e., Group 1-4, the blank experiment), however, the concentrations of the alcohol substance and the metal salt were 0% and 0M respectively.

TABLE 1

| Group | Alcohol substance | Metal salt | Binding effect (%) | Recovery rate (%) |
|---|---|---|---|---|
| 1-1 | 72% EtOH | 0.05M LiCl | 81 | 22 |
| 1-2 | 72% EtOH | 0.05M NaOAc | 94 | 76 |
| 1-3 | 72% EtOH | 0.05M NaCl | 86 | 57 |
| 1-4 | 0% EtOH | 0M salt | N/A* | N/A* |

*Not available.

It can be known from the results in Table 1 that the binding effect is greater than 90% for all the combinations between the 72% ethanol and the different 0.05M metal salts. In particular, the combination of 72% ethanol and 0.05M NaOAc produced the optimal effect.

Comparative Example 2

Referring to Table 2, wherein a whole blood sample of a fixed volume was used, 0.05M, 0.1M, 0.5M, 1.0M, and 2M sodium acetate or potassium acetate (KOAc) was used as the metal salt solution in the foregoing embodiments to work in conjunction with an alcohol substance whose concentration ranges from 10% to 72% by weight (Group 2-1 to 2-8). On the other hand, Group 2-9 is the control group (i.e., blank experiment), wherein the concentrations of the alcohol substance and the potassium acetate are 0% and 0M respectively.

More specifically, whole blood samples of the same volume were treated with a lysis buffer to obtain cell lysates. Metal salt solutions of the aforesaid different concentrations and chaotropic agents of different concentrations by weight were added to the cell lysates along with a magnetic cellulose material and mixed thoroughly with the cell lysates. The mixture was washed with 70% isopropanol as the washing buffer and then eluted with pH 8.0, 10 mM Tris-HCl as the elution buffer, thereby recovering the DNA from the sample. Then, the DNA concentration of the sample in each group was measured in the unit of ng/μl. In addition, the absorbance ratios of the recovered DNA product in each group between 260 nm and 280 nm (i.e., the O.D.260/280 ratio) and between 260 nm and 230 nm (i.e., the O.D.260/230 ratio) were measured to determine the purity of the recovered DNA in each group.

TABLE 2

| Group | Alcohol substance | Metal salt (Li salt, Na salt, or K salt) | DNA product concentration (ng/μl) | O.D. 260/280 ratio | O.D. 260/230 ratio |
|---|---|---|---|---|---|
| 2-1 | 50% isopropanol | 0.5M KOAc | 22.12 | 1.52 | 0.21 |
| 2-2 | 50% isopropanol | 1M KOAc | 28.99 | 1.67 | 0.24 |
| 2-3 | 72% isopropanol | 0.05M NaOAc | 60.92 | 1.64 | 0.41 |
| 2-4 | 25% isopropanol | 1M KOAc | 32.23 | 1.5 | 0.21 |
| 2-5 | 25% isopropanol | 2M KOAc | 27.12 | 1.61 | 0.24 |
| 2-6 | 10% | 0.1M NaOAc, | 34.06 | 1.52 | 0.17 |
| 2-7 | Isopropanol 50% isopropanol | pH 5.0 0.05M KOAc | 19.49 | 1.91 | 0.07 |
| 2-8 | 25% isopropanol | 0.05M KOAc | 24.63 | 1.9 | 0.24 |
| 2-9 | 0% isopropanol | 0M KOAc | 0 | N/A* | N/A* |

*Not available.

It can be known from the results in Table 2 that, for all the combinations between the 10% to 72% alcohol substance and the 0.05M to 2M metal salts, the final DNA products are of high purity, with low protein content (O.D.260/280 ratio>1.5) as well as low RNA content (O.D.260/230 ratio<0.5) in the products. In addition, while this comparative example only shows the experiment results corresponding to the different metal salts used in combination with the 10% to 72% alcohol substance, other experiments have shown that a good isolation effect and high DNA product purity were achieved when the concentration of the alcohol substance was raised to 80%; furthermore, chaotropic agents or reagents with pH values ranging from 5.0 to 7.5 were proven to be equally capable of promoting isolation of a nucleic acid from non-nucleic acid substances and of promoting binding of the nucleic acid to the magnetic cellulose material.

Therefore, the chaotropic agent, the reagent including a chaotropic agent and a metal salt, the reagent kit including a chaotropic agent, the chaotropic agent for isolating a nucleic acid by use of a magnetic cellulose material, the reagent for isolating a nucleic acid by use of a magnetic cellulose material, and the reagent kit for isolating a nucleic acid by use of a magnetic cellulose material as disclosed herein work effectively with a solid-phase carrier containing a magnetic cellulose material to produce good isolation and purification effects.

Embodiment 7

Embodiment 7 of the present invention is a method for isolating a nucleic acid by use of a magnetic cellulose material. The method includes providing a nucleic acid-containing sample and preparing a reagent and a magnetic cellulose material for use with the reagent. The reagent includes a metal salt and a chaotropic agent, wherein the chaotropic agent includes an alcohol substance and a substrate solution. The concentration of the metal salt, as well as the concentrations and pH values of the alcohol substance and the substrate solution, is the same as in Embodiment 2 and therefore is not repeated herein. The following two paragraphs describe only the unique features of the present embodiment.

First, a sample containing a nucleic acid, such as a cell lysate, is provided, wherein the cell lysate can be obtained from a culture solution containing cells or bacteria, a tissue sample, a whole blood sample, etc. In addition, a reagent and a magnetic cellulose material for use with the reagent are prepared. The reagent includes a lithium salt, sodium salt, or potassium salt having a predetermined concentration and a chaotropic agent, wherein the chaotropic agent includes an alcohol substance and a substrate solution. The reagent and magnetic cellulose material are added to and mixed with the nucleic acid-containing sample such that the sample is mixed with the magnetic cellulose material. As the substrate solution adjusts the concentration of the alcohol substance to an appropriate level, the chaotropic agent in the reagent breaks the hydrogen bonding, Van der Waals interactions, or hydrophobic effects between the nucleic acid and the environment in which the nucleic acid is located, thereby isolating the DNA in the sample from the non-nucleic acid substances. The DNA in the sample then binds and is adsorbed to the magnetic cellulose material to form a complex.

The method may further include providing a washing buffer for washing off the non-nucleic acid substances adsorbed to the complex formed by the DNA and the magnetic cellulose material. The method may also include providing an elution buffer which, after the aforesaid washing process is complete, washes the DNA off the magnetic cellulose material such that the DNA is eluted into the elution buffer and ready to be recovered. Detailed experiment results are presented in Comparative Example 3 that follows.

Comparative Example 3

The steps performed are as follows:

(a) Add 200 µl of lysis buffer and 20 µl of 10 mg/ml Proteinase K into 200 µl of whole blood sample. Mix well to produce a cell lysate.

(b) Add 500 µl of reagent into the cell lysate, wherein the reagent includes 10% to 72% isopropanol, 0.05M to 2.0M sodium acetate or potassium acetate, and a solid-phase carrier containing the magnetic cellulose material, and wherein the reagent has a pH value smaller than or equal to 6.0. As a result, the chromosome DNA in the sample binds to the solid-phase carrier.

(c) Wash off the non-nucleic acid substances, which do not bind to the solid-phase carrier, with 1 ml of washing buffer. The washing buffer contains either 70% isopropanol or 20% PEG6000 and 2M potassium acetate.

(d) Isolate the chromosome DNA from the solid-phase carrier, with 100 µl of pH 8.0, 10 mM Tris-HCl as the elution buffer.

Afterward, the DNA concentration of the sample in each group is measured in the unit of ng/µl. Furthermore, the absorbance ratios of the recovered DNA product in each group between 260 nm and 280 nm (i.e., the O.D.260/280 ratio) and between 260 nm and 230 nm (i.e., the O.D.260/230 ratio) are measured to determine the purity of the recovered DNA in each group.

TABLE 3

| Group | Alcohol substance | Metal salt (Li salt, Na salt, or K salt) | DNA product concentration (ng/µl) | O.D. 260/280 ratio | O.D. 260/230 ratio |
|---|---|---|---|---|---|
| 3-1 | 50% isopropanol | 0.5M KOAc | 11.31 | 2.93 | 0.17 |
| 3-2 | 50% isopropanol | 1M KOAc | 13.31 | 1.72 | 0.19 |
| 3-3 | 72% isopropanol | 0.05M NaOAc | 28.56 | 1.53 | 0.22 |
| 3-4 | 25% isopropanol | 1M KOAc | 9.42 | 1.58 | 0.12 |
| 3-5 | 25% isopropanol | 2M KOAc | 9.76 | 1.77 | 0.17 |
| 3-6 | 10% Isopropanol | 0.1M NaOAc, pH 5.0 | 5.75 | 0.96 | 0.06 |
| 3-7 | 72% isopropanol | 0.05M NaOAc | 68.19 | 1.71 | 0.42 |
| 3-8 | 50% isopropanol | 0.05M KOAc | 19.49 | 1.91 | 0.07 |
| 3-9 | 25% isopropanol | 0.05M KOAc | 24.63 | 1.9 | 0.24 |
| 3-10 | 0% isopropanol | 0M KOAc | 0 | N/A* | N/A* |

*Not available.

According to the results shown in Table 3, at least 5 ng/µl of chromosome DNA was obtained with the 10% to 72% alcohol substance and the 0.05M to 2M metal salts. Besides, the DNA products are of high purity, for generally speaking, the chromosome DNA obtained has low protein content (O.D.260/280 ratio>1.5) as well as low RNA content (O.D.260/230 ration<0.5). In addition, while this comparative example only shows the experiment results corresponding to the different metal salts used in combination with the 10% to 72% alcohol substance, other experiments have shown that a good isolation effect and high DNA product purity were achieved when the concentration of the alcohol substance was raised to 80%; furthermore, chaotropic agents or reagents with pH values ranging from 5.0 to 7.5 were proven to be equally capable of promoting isolation of a nucleic acid from non-nucleic acid substances and of promoting binding of the nucleic acid to the magnetic cellulose material.

Therefore, the method for isolating a nucleic acid by use of a magnetic cellulose material, the method for binding a nucleic acid to a magnetic cellulose material, the method for isolating a nucleic acid, and the method for purifying a chromosome DNA as disclosed herein work effectively with a solid-phase carrier containing a magnetic cellulose material to produce good isolation and purification effects.

What is claimed is:

1. A reagent composition for initiating the separation of the nucleic acid DNA from non-nucleic acid substances by initiating the lysis of a cellular source wherein said composition also promotes the adsorption of nucleic acids onto magnetic cellulose paper, particles or beads, the composition comprising an aqueous solution of a chaotropic univalent metal salt and an alcohol or an alcoholic mixture selected from the group consisting of ethanol, isopropanol, and an arbitrarily selected mixture of ethanol and isopropanol, wherein the chaotropic univalent metal salt is selected from lithium chloride (LiCl), sodium acetate (NaOAc), sodium chloride (NaCl), and potassium acetate (KOAc), and further with the optional presence of proteinase K.

2. The reagent composition of claim 1, wherein the alcohol substance has a concentration ranging approximately from 10% to 80%.

3. The reagent composition of claim 1, wherein the metal salt has a concentration ranging approximately from 0.05M to 2.0M.

4. The reagent composition of claim 1, wherein the substrate solution has a pH value ranging approximately from 5.0 to 7.5.

5. The reagent composition of claim 1, wherein the solid-phase carrier is magnetic cellulose bead formed from a magnetic cellulose composition.

6. A reagent kit for isolating a nucleic acid DNA from non-nucleic acid substances, the reagent kit comprising a reagent composition, a solid-phase carrier, a washing buffer, and an elution buffer, wherein the reagent composition is as defined in claim 1.

7. The reagent kit of claim 6, wherein the alcohol substance has a concentration ranging approximately from 10% to 80%.

8. The reagent kit of claim 6, wherein the wherein the metal salt has a concentration ranging approximately from 0.05M to 2.0M.

9. The reagent kit of claim 6, wherein the substrate solution has a pH value ranging approximately from 5.0 to 7.5.

10. The reagent kit of claim 6, wherein the solid-phase carrier is magnetic cellulose beads.

11. A method for isolating a nucleic acid from non-nucleic acid substances from a cellular source is selected from a culture of cells or bacteria in solution, a solid tissue sample and a whole blood sample, comprising the following steps:
(1) providing a reagent composition and a solid-phase carrier as defined in claim 6;
(2) contacting the reagent composition and the solid-phase carrier to a sample containing the nucleic acid and the non-nucleic acid substances;
(3) separating the magnetic cellulose-nucleic acid composition by application of a magnetic field to the reaction vessel or reaction container, separating or withdrawing the liquid phase, and washing one or more times the solid support with the wash buffer as defined in claim 6;
(4) elution of the adsorbed nucleic acids from the solid support by contacting the solid support with the elution buffer as defined in claim 6; and
(5) isolation of the nucleic acid by conventional methods known in the art.

12. The method for isolating a nucleic acid from non-nucleic acid substances according to claim 11, wherein the alcohol substance has a concentration ranging approximately from 10% to 80%.

13. The method for isolating a nucleic acid from non-nucleic acid substances according to claim 11, wherein the metal salt has a concentration ranging approximately from 0.05M to 2.0M.

14. The method for isolating a nucleic acid from non-nucleic acid substances according to claim 11, wherein the substrate solution has a pH value ranging approximately from 5.0 to 7.5.

15. The method for isolating a nucleic acid from non-nucleic acid substances according to claim 11, wherein the sample is a cell lysate.

* * * * *